(12) United States Patent
Lubisch et al.

(10) Patent No.: US 6,448,254 B1
(45) Date of Patent: Sep. 10, 2002

(54) SUBSTITUTED AMIDES, THEIR PRODUCTION AND THEIR USE

(75) Inventors: Wilfried Lubisch, Heidelberg; Achim Möller, Grünstadt; Hans-Jörg Treiber, Brühl; Monika Knopp, Ludwigshafen, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/647,677

(22) PCT Filed: Apr. 19, 1999

(86) PCT No.: PCT/EP99/02618

§ 371 (c)(1),
(2), (4) Date: Oct. 3, 2000

(87) PCT Pub. No.: WO99/54294

PCT Pub. Date: Oct. 28, 1999

(30) Foreign Application Priority Data

Apr. 20, 1998 (DE) .......................... 198 18 614

(51) Int. Cl.[7] ............................................ C07C 311/21
(52) U.S. Cl. .................. 514/267; 546/334; 546/154; 514/357; 514/312; 514/561; 514/562; 544/249; 562/442; 562/427
(58) Field of Search ................................ 546/334, 154; 514/357, 312, 267, 561, 562; 544/249; 562/442, 427

(56) References Cited

U.S. PATENT DOCUMENTS 5,289,954 A   3/1994   Brueggendick ............. 222/409

FOREIGN PATENT DOCUMENTS

| CA | 1335079 | 4/1995 |
|---|---|---|
| EP | 520 336 | 12/1992 |
| EP | 611 756 | 8/1994 |
| WO | 91/09801 | 7/1991 |
| WO | 92/11850 | 7/1992 |
| WO | 94/00095 | 1/1994 |
| WO | 94/19320 | 9/1994 |
| WO | 95/00535 | 1/1995 |
| WO | 96/39194 | 12/1996 |
| WO | 97/10231 | 3/1997 |
| WO | 97/21690 | 6/1997 |
| WO | 92/12140 | 7/1997 |

OTHER PUBLICATIONS

Leung et al. Protease inhibitors: current status and future prospects J. Med. Chem. 43(3) :305–341, 2000.*
Bio.&Bio.Res.Com.vol. 158,1989,McGowan.
J.Med.Chem.1992,35,216–220,Angliker et al.
Chem.Soc.ofJP,pp 191–194,1990, Matsueda et al.
TIBS16,Apr. 1991,Mehdi,150–153.
Bio.Med.Chem.Lts. vol.7, No. 3,287–290, 1997, Chatterjee.
Bio.Med.Chem.Ltr.vol. 6,No. 13,1619–1622,1996,Chatterjee.
J.Med.Che.1993,36,3472–3480,Li et al.
J.Med.Chem.1994,37,2918–2929, Harbeson et al..
Burkhart et al.

* cited by examiner

Primary Examiner—Mukund I. Shah
Assistant Examiner—Hong Liu
(74) Attorney, Agent, or Firm—Keil & Weinkauf

(57) ABSTRACT

Amides of the general formula I

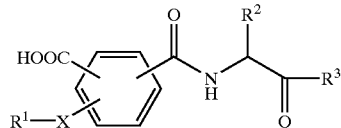

and their tautomeric and isomeric forms, possible enantiomeric and diastereomeric forms, as well as possible physiologically tolerable salts, in which the variables have the following meanings:

R1 [sic] can be $C_1$–$C_6$-alkyl, phenyl, naphthyl, quinolyl, pyridyl, pyrimidyl, pyridazyl, quinazolyl and quinoxalyl, where the rings can additionally be substituted by up to 2 radicals R4 [sic], and R2 [sic] is —$(CH_2)_m$—R8 [sic], where R8 [sic] can be phenyl, cyclohexyl- or indolyl and m=1 to 6, and X is a bond, —$CH_2$—, —$CH_2CH_2$—, —CH=CH—, —C≡C—, —CONH—, —$SO_2NH$— [sic], and and [sic]

R1—X [sic] together are also

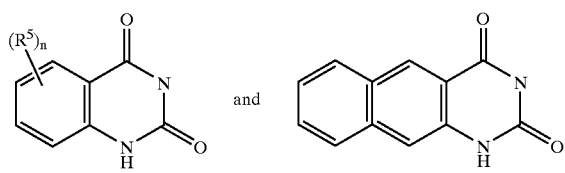

and

R3 [sic] is hydrogen and CO—NR6R7 [sic],

R4 [sic] is hydrogen, C1–C4-alkyl [sic], which is branched and unbranched, and —O—C1–C4-alkyl [sic];

R5 [sic] is hydrogen, C1–C4-alkyl [sic], which is branched or unbranched, and —O—C1–C4-alkyl [sic];

R6 [sic] is hydrogen, $C_1$–$C_6$-alkyl, which is branched and unbranched, and

R7 [sic] is hydrogen, $C_1$–$C_6$-alkyl, which is branched or unbranched, and n is is [sic] a number 0, 1 or 2.

3 Claims, No Drawings

SUBSTITUTED AMIDES, THEIR PRODUCTION AND THEIR USE

The present invention relates to novel amides, which are inhibitors of enzymes, in particular cysteine proteases, such as calpain (=calcium-dependent cysteine proteases) and its isoenzymes and cathepsins, for example B and L.

Calpains are intracellular, proteolytic enzymes from the so-called cysteine proteases group and are found in many cells. Calpains are activated by an increased calcium concentration, a differentiation being made between calpain I or µ-calpain, which is activated by µ-molar concentrations of calcium ions, and calpain II or m-calpain, which is activated by m-molar concentrations of calcium ions (P. Johnson, Int. J. Biochem. 1990, 22(8), 811–22). Still further calpain isoenzymes are postulated today (K. Suzuki et al., Biol. Chem. Hoppe-Seyler, 1995, 376(9), 523–9).

It is suspected that calpains play an important part in various physiological processes. These include cleavage of regulatory proteins such as protein kinase C, cytoskeletal proteins such as MAP 2 and spectrin, muscle proteins, protein breakdown in rheumatoid arthritis, proteins in the activation of platelets, neuropeptide metabolism, proteins in mitosis and others which are listed in M. J. Barrett et al., Life Sci. 1991, 48, 1659–69 and K. K. Wang et al., Trends in Pharmacol. Sci., 1994, 15, 412–9.

Increased calpain levels have been measured in various pathophysiological processes, for example ischemias of the heart (e.g. cardiac infarct), of the kidney or of the central nervous system (e.g. "stroke"), inflammations, muscular dystrophy, cataracts of the eyes, injuries to the central nervous system (e.g. trauma), Alzheimer's disease etc. (see K. K. Wang, above). A relationship of these diseases with increased and lasting intracellular calcium levels is suspected. As a result, calcium-dependent processes are overactivated and are no longer subject to physiological regulation. Accordingly, overactivation of calpains can also initiate pathophysiological processes.

It was therefore postulated that inhibitors of the calpain enzymes can be useful for the treatment of these diseases. Various investigations confirm this. Thus, Seung-Chyul Hong et al., Stroke 1994, 25(3), 663–9 and R. T. Bartus et al., Neurological Res. 1995, 17, 249–58 have shown a neuroprotective action of calpain inhibitors in acute neurodegenerative disorders or ischemias, such as occur after cerebral stroke. Likewise, after experimental brain traumata, calpain inhibitors improved recovery from the memory power deficits and neuromotor disorders which occurred (K. E. Saatman et al. Proc. Natl. Acad. Sci. USA, 1996, 93, 3428–3433). C. L. Edelstein et al., Proc. Natl. Acad. Sci. USA, 1995, 92, 7662–6, found a protective action of calpain inhibitors on kidneys damaged by hypoxia. Yoshida, Ken Ischi et al., Jap. Circ. J. 1995, 59(1), 40–8, were able to show favorable effects of calpain inhibitors after cardiac damage which was produced by ischemia or reperfusion. Since calpain inhibitors inhibit the release of the β-AP4 protein, potential use as a therapeutic for Alzheimer's disease was proposed (J. Higaki et al., Neuron, 1995, 14, 651–59). The release of interleukin-1α is also inhibited by calpain inhibitors (N. Watanabe et al., Cytokine 1994, 6(6), 597–601). It was furthermore found that calpain inhibitors show cytotoxic effects on tumor cells (E. Shiba et al., 20th Meeting Int. Ass. Breast Cancer Res., Sendai Jp, Sep. 25–28 1994, Int. J. Oncol. 5 (Suppl.), 1994, 381).

Further possible uses of calpain inhibitors are listed in K. K. Wang, Trends in Pharmacol. Sci., 1994, 15, 412–8.

Calpain inhibitors have already been described in the literature. These are mainly, however, either irreversible or peptide inhibitors. As a rule, irreversible inhibitors are alkylating substances and have the disadvantage that they react nonselectively in the body or are unstable. Thus these inhibitors often show undesirable side effects, such as toxicity, and are accordingly restricted in their use or unutilizable. Among the irreversible inhibitors can be included, for example, the epoxides E 64 (E. B. McGowan et al., Biochem. Biophys. Res. Commun. 1989, 158, 432–5), α-haloketones (H. Angliker et al., J. Med. Chem. 1992, 35, 216–20) or disulfides (R. Matsueda et al., Chem. Lett. 1990, 191–194).

Many known reversible inhibitors of cysteine proteases, such as calpain, are peptide aldehydes, in particular dipeptide and tripeptide aldehydes such as, for example, Z-Val-Phe-H (MDL 28170) (S. Mehdi, Trends in Biol. Sci. 1991, 16, 150–3). Under physiological conditions, peptide aldehydes have the disadvantage that they are often unstable on account of the great reactivity, can be rapidly metabolized and are prone to nonspecific reactions which can be the cause of toxic effects (J. A. Fehrentz and B. Castro, Synthesis 1983, 676–78.

In JP 08183771 (CA 1996, 605307) and in EP 520336, aldehydes which are derived from 4-piperidinoylamides and 1-carbonylpiperidino-4-ylamides have been described as calpain inhibitors. However, the aldehydes claimed here, which are derived from heteroaromatically substituted amides of the general structure I, have previously been described. Other aldehyde derivatives have been described in Chatterjee et al. Bioorganic & Medicinal Chemistry Letters, 1997, 7, 287–290, Chatterjee et al. Bioorganic & Medicinal Chemistry Letters 1996, 6, 1619–1622, WO 97/10231 and WO 97/21690.

Peptide ketone derivatives are also inhibitors of cysteine proteases, in particular calpains. Thus, for example, in the case of serine proteases ketone derivatives are known as inhibitors, the keto group being activated by an electron-withdrawing group such as CF3 [sic]. In the case of cysteine proteases, derivatives with ketones activated by CF3 [sic] or similar groups are not very active or inactive (M. R. Angelastro et al., J. Med. Chem. 1990, 33, 11–13). Surprisingly, in the case of calpain hitherto only ketone derivatives, in which, on the one hand, leaving groups in the α-position cause an irreversible inhibition and, on the other hand, a carboxylic acid derivative activates the keto group, were found to be effective inhibitors (see M. R. Angelastro et al., see above; WO 92/11850; WO 92,12140; WO 94/00095 and WO 95/00535). However, of these ketoamides and ketoesters, virtually only peptide derivatives have been described as effective (Zhaozhao Li et al., J. Med. Chem. 1993, 36, 3472–80; S. L. Harbenson et al., J. Med. Chem. 1994, 37, 2918–29 and, see above, M. R. Angelastro et al.). Only in Chatterjee et al. (see above) has a xanthene derivative of a ketobenzamide been described as a calpain inhibitor.

Ketobenzamides are already known in the literature. Thus the keto ester PhCO—Abu—COOCH$_2$CH$_3$ was described in WO 91/09801, WO 94/00095 and 92/11850. The analogous phenyl derivative Ph—CONH—CH(CH$_2$Ph)—CO—COOCH$_3$ was found in M. R. Angelastro et al., J. Med. Chem. 1990, 33, 11–13 to be, however, only a weak calpain inhibitor. This derivative is also described in J. P. Burkhardt, Tetrahedron Lett., 1988, 3433–36. The significance of the substituted benzamides, however, has never been investigated until now.

In a number of therapies, such as stroke, the active compounds are administered intravenously as an infusion solution. For this purpose, it is necessary to have at one's disposal substances, in this case calpain inhibitors, which have sufficient water-solubility so that an infusion solution can be prepared. Many of the calpain inhibitors described, however, have the disadvantage that they only show a small or no water-solubility and are thus not suitable for intravenous administration. Active compounds of this type can only be administered using auxiliaries which are intended to impart water-solubility (cf. R. T. Bartus et al. *J. Cereb. Blood Flow Metab.* 1994, 14, 537–544). These auxiliaries, for example polyethylene glycol, frequently, however, have side effects or are even intolerable. A nonpeptide calpain inhibitor which is accordingly water-soluble without auxiliaries and therefore can probably be administered with better tolerability thus has a great advantage. Highly efficacious nonpeptide calpain inhibitors having sufficient water-solubility have not previously been described and would therefore be novel.

In the present invention, nonpeptide aldehydes, ketocarboxylic acid esters and ketoamide derivatives are described. These compounds are novel and surprisingly show the possibility of obtaining potent nonpeptide inhibitors of cysteine proteases, such as, for example, calpain, by incorporation of rigid structural fragments. Furthermore, in the case of the present compounds of the general formula I, which all carry at least one aliphatic amine radical, salt bonds with acids are possible. This leads to an improved water-solubility and therefore the compounds show the desired profile for intravenous administration, such as is necessary, for example, in stroke therapy.

The present invention relates to substituted amides of the general formula I

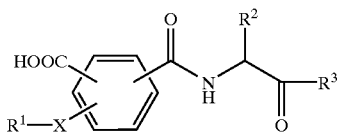

and their tautomeric and isomeric forms, possible enantiomeric and diastereomeric forms, as well as possible physiologically tolerable salts, in which the variables have the following meanings:

R1 [sic] can be $C_1$–$C_6$-alkyl, phenyl, naphthyl, quinolyl, pyridyl, pyrimidyl, pyridazyl, quinazolyl and quinoxalyl, where the rings can additionally be substituted by up to 2 radicals R4 [sic], and R2 [sic] is —(CH$_2$)$_m$—R8 [sic], where R8 [sic] can be phenyl, cyclohexyl- [sic] or indolyl and m=1 to 6, and X is a bond, —CH$_2$—, —CH$_2$CH$_2$—, —CH=CH—, —C≡C—, —CONH—, —SO$_2$NH— [sic], and and [sic]

R1—X [sic] together are also

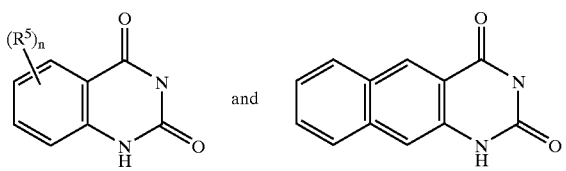

and

R3 [sic] is hydrogen and CO—NR6R7 [sic],

R4 [sic] is hydrogen, C1–C4-alkyl [sic], which is branched and unbranched, and —O—C1–C4-alkyl [sic];

R5 [sic] is hydrogen, C1–C4-alkyl [sic], which is branched or unbranched, and —O—C1–C4-alkyl [sic];

R6 is hydrogen, $C_1$–$C_6$-alkyl, which is branched and unbranched, and

R7 [sic] is hydrogen, $C_1$–$C_6$-alkyl, which is branched or unbranched, and n is is [sic] a number 0, 1 or 2.

The compounds of the formula I can be employed as racemates, as enantiomerically pure compounds or as diastereomers. If enantiomerically pure compounds are desired, these can be obtained, for example, by carrying out a classical racemate resolution with the compounds of the formula I or their intermediates using a suitable optically active base or acid. On the other hand, the enantiomeric compounds can also be prepared by using commercially obtainable compounds, for example optically active amino acids such as phenylalanine, tryptophan and tyrosine.

The present invention also relates to compounds which are mesomeric or tautomeric with compounds of the formula I, for example those in which the aldehyde or keto group of the formula I is present as an enol tautomer.

The present invention further relates to the physiologically tolerable salts of the compounds I, which can be obtained by reaction of compounds I with a suitable acid or base. Suitable acids and bases are listed, for example, in Fortschritte der Arzneimittelforschung [Advances in Drug Research], 1996, Birkhäuser Verlag, Vol. 10, pp. 224–285. These include, for example, hydrochloric acid, citric acid, tartaric acid, lactic acid, phosphoric acid, methanesulfonic acid, acetic acid, formic acid, maleic acid, fumaric acid etc. or sodium hydroxide, lithium hydroxide, potassium hydroxide and tris.

The amides I according to the invention, which carry an aldehyde group, can be prepared in various ways, which have been outlined in synthesis scheme 1.

Synthesis scheme 1

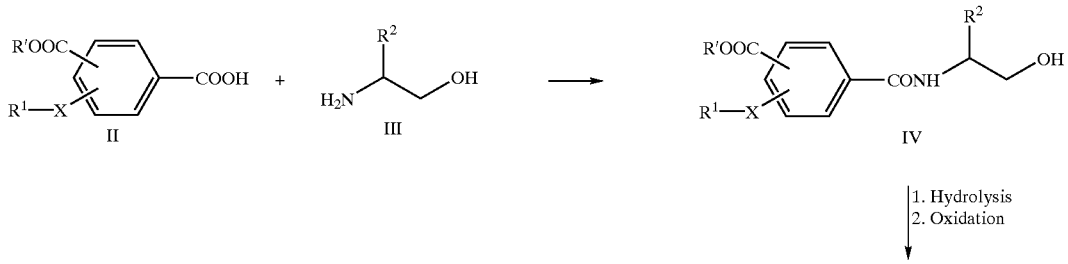

1. Hydrolysis
2. Oxidation

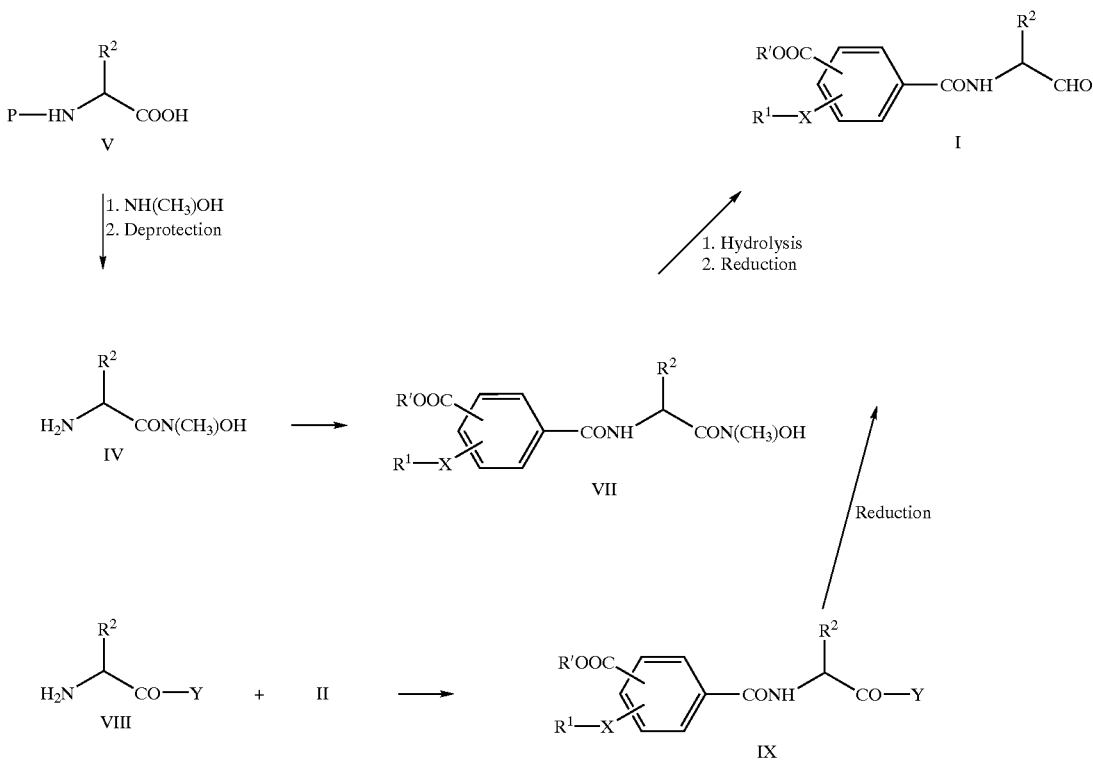

Carboxylic acids II are linked to suitable aminoalcohols III to give the corresponding amides IV. Use is made here of customary peptide coupling methods, which are mentioned either in C. R. Larock, Comprehensive Organic Transformations, VCH Publisher, 1989, page 972f. or in Houben-Weyl, Methoden der organischen Chemie [Methods of Organic Chemistry], 4th Edition, E5, Chap. V. The reaction is preferably carried out using "activated" acid derivatives of II, the acid group COOH being converted into a group COL. L is a leaving group such as, for example, Cl, imidazole or N-hydroxybenzotriazole. This activated acid is then converted to the amides IV using amines. The reaction is carried out in anhydrous, inert solvents such as methylene chloride, tetrahydrofuran and dimethylformamide at temperatures from −20 to +250° C. [sic].

These carboxylic acid esters IV (R'=O-alkyl) are converted into the acids IV (R'=H) using acids such as triflouroacetic [sic] acid or hydrochloric acid or bases such as lithium hydroxide, sodium hydroxide or potassium hydroxide in aqueous medium or in mixtures of water and organic solvents such as alcohols or tetrahydrofuran at room temperature or elevated temperatures, such as 25–100° C.

These derivatives IV (R'=H) which are obtained can be oxidized to the aldehyde derivatives I according to the invention. It is possible to use various customary oxidation reactions for this (see C. R. Larock, Comprehensive organic Transformations, VCH Publisher, 1989, page 604 f.) such as, for example, Swern and Swern-analogous oxidations (T. T. Tidwell, Synthesis 1990, 857–70), sodium hypochlorid [sic]/TEMPO (S. L. Harbenson et al., see above) or Dess-Martin (J. Org. Chem. 1983, 48, 4155). Preferably, the reaction here is carried out in inert aprotic solvents such as dimethylformamide, tetrahydrofuran or methylene chloride using oxidants such as DMSO/pyxSO₃ or DMSO/oxalyl chloride at temperatures from −50 to +250° C. [sic], depending on the method (see above references).

Alternatively, the carboxylic acid II can be reacted with aminohydroxamic acid derivatives VI to give benzamides VII. In this case, use is made of the same reaction procedure as in the preparation of IV. The hydroxamic [lacuna] derivatives VI are obtainable from the protected amino acids V by reaction with a hydroxylamine. In this process, use is also made here of an amide preparation process which has already been described. The removal of the protective group X, for example Boc, is carried out in a customary manner, for example using trifluoroacetic acid. The amidohydroxamic acids VII thus obtained can be converted into the aldehydes I according to the invention by reduction. In this process, use is made, for example, of lithium aluminum hydride as a reductant at temperatures from −60 to 0° C. [sic] in inert solvents such as tetrahydrofuran or ether.

Analogously to the last process, carboxylic acids or acid derivatives, such as esters IX (Y=COOR', COSR') can also be prepared, which can likewise be converted into the aldehydes I according to the invention by reduction. These processes are listed in R. C. Larock, Comprehensive Organic Transformations, VCH Publisher, 1989, pages 619–26.

The preparation of the substituted amides I according to the invention, [lacuna] carry a ketoamide or ketoester group, can be carried out in various ways, which have been outlined in Synthesis scheme 2.

Synthesis scheme 2

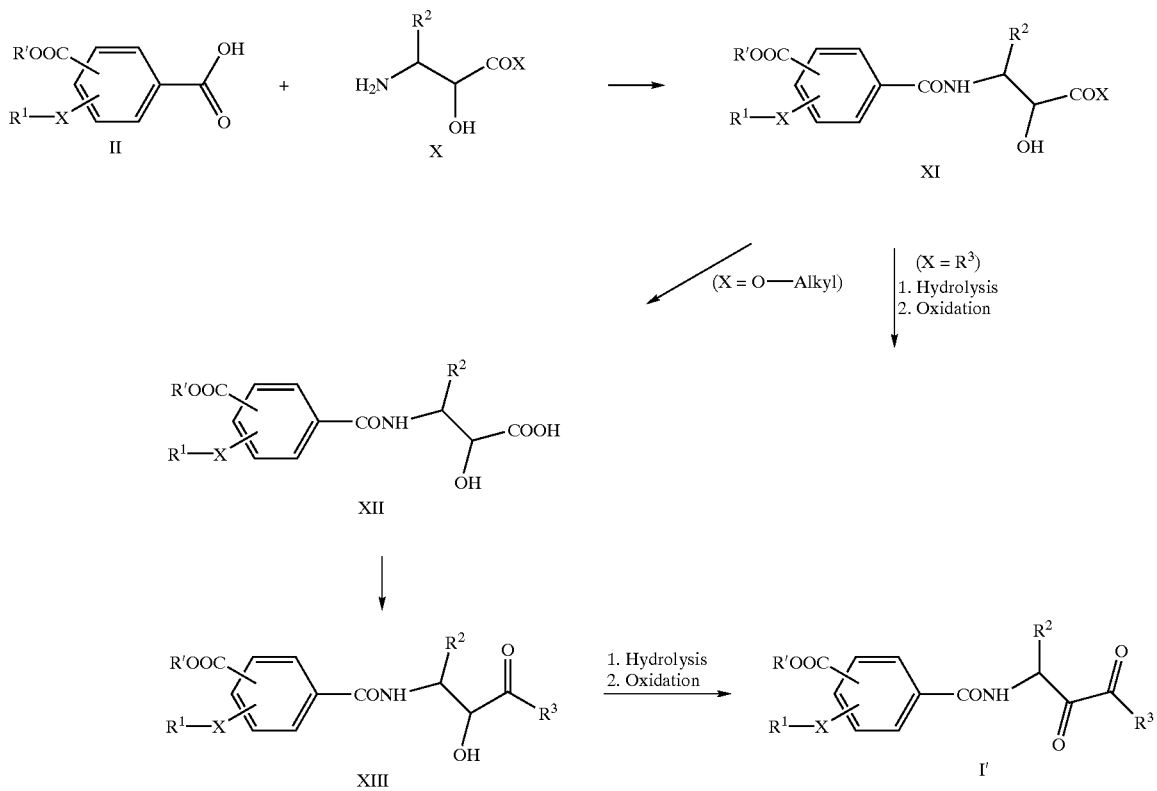

The carboxylic acids II are reacted with aminohydroxy-carboxylic acid derivatives X (for preparation of XI see S. L. Harbenson et al., *J. Med. Chem.* 1994, 37, 2918–29 or J. P. Burkhardt et al. *Tetrahedron Lett.* 1988, 29, 3433–3436) under customary peptide coupling methods (see above, Houben-Weyl), amides XIII being obtained.

These carboxylic acid esters XIII (R'=O-alkyl) are converted into the acids XIII (R'=H) using acids such as trifluoroacetic acid or hydrochloric acid or bases such as lithium hydroxide, sodium hydroxide or potassium hydroxide in aqueous medium or in mixtures of water and organic solvents such as alcohols or tetrahydrofuran at room temperature or elevated temperatures, such as 25–100° C.

The derivatives XIII obtained can be oxidized to the ketocarboxylic acid derivatives I' according to the invention. Use can be made for this of various customary oxidation reactions (see C. R. Larock, *Comprehensive Organic Transformations*, VCH Publisher, 1989, page 604 f.) such as, for example, Swern and Swern-analogous oxidations, preferably dimethyl sulfoxide/pyridine-sulfur trioxide complex in solvents such as methylene chloride or tetrahydrofuran, if appropriate with addition of dimethyl sulfoxide, at room temperature or temperatures of −50 to 25° C (T. T. Tidwell, *Synthesis* 1990, 857–70) or sodium hypochloride [sic]/TEMPO (S. L. Harbenson et al., see above).

If XI are α-hydroxy esters (X=O-alkyl), these can be hydrolyzed to carboxylic acids XII, the reaction being carried out analogously to the above methods, but preferably using lithium hydroxide in water/tetrahydrofuran mixtures at room temperature, it being necessary to take into consideration, however, that in this case, for the protective group R', a radical is selected such as, for example, tert-butyl-O, which allows the selective cleavage of one of the two ester groups. The preparation of other amides XIII is carried out by reaction with amines under coupling conditions which have already been described. The alcohol derivative XIII can be oxidized again to give ketocarboxylic acid derivatives I' according to the invention.

The preparation of the carboxylic acid esters II has already been described in some cases or is carried out according to customary chemical methods.

Compounds in which X is a bond are prepared by customary aromatic coupling, for example the Suzuki coupling with boric acid derivatives and halides under palladium catalysis or copper-catalyzed coupling of aromatic halides. The alkyl-bridged radicals (X=—$(CH_2)_m$—) can be prepared by reduction of the analogous ketones or by alkylation of the organolithium, e.g. ortho-phenyloxazolidines, or other organometal compounds (cf. I. M. Dordor et al., J. Chem. Soc. Perkin Trans. I, 1984, 40 1247–52).

Alkene- and alkyne-bridged compounds are prepared, for example, by Heck reaction from aromatic halides and appropriate alkenes and alkynes (cf. I. Sakamoto et al., Chem. Pharm. Bull., 1986, 45 34, 2754–59).

Amides and sulfonamides are prepared from the amines and acid derivatives analogously to the methods described above.

Alternatively, compounds of the general formula I can also be synthesized by modifying or exchanging the reaction sequences which are listed in schemes 1 and 2. Thus, for example, a sulfonamide I (R1X [sic]=$RSO_2NH$) can be prepared from a derivative IV (R1X [sic]=$NO_2$) by reducing the nitro group to the amine catalytically in a customary manner using hydrogen on a catalyst, such as palladium/carbon, and then reacting the resulting amine with a sulfonyl chloride to give a derivative IV (R1X [sic]=RSO₂NH). Further reaction to give I is carried out, as shown in the scheme, by ester hydrolysis and oxidation. Analogously, the intermediates IV and XI (R1X [sic]=chemical groups such as nitro, amino, halogen etc.), can be converted into derivatives in which R1X [sic] corresponds to further radicals mentioned in the general claim. The reactions are carried out a here analogously to the processes described above or analogously to general or customary methods.

The heterocyclically substituted amides I contained in the present invention are inhibitors of cysteine proteases, in particular cysteine proteases such as the calpains I and II and cathepsins B and L.

The inhibitory action of the heterocyclically substituted amides I was determined using enzyme tests customary in the literature, a concentration of the inhibitor at which 50% of the enzyme activity is inhibited (=IC50 [sic]) being determined as a scale of action. The amides I were measured in this manner for inhibitory action of calpain I, calpain II and cathepsin B.

Cathepsin B Test

The cathepsin B inhibition was determined analogously to a method by S. Hasnain et al., *J. Biol. Chem.* 1993, 268, 235–40.

2 µL of an inhibitor solution, prepared from inhibitor and DMSO (final concentrations: 100 µM to 0.01 µM) are added to 88 µL of cathepsin B (cathepsin B from human liver (Calbiochem), diluted to 5 units in 500 µM buffer). This mixture is preincubated at room temperature (25° C.) for 60 minutes and the reaction is then started by addition of 10 µL of 10 mM Z-Arg-Arg-pNA (in buffer with 10% DMSO). The reaction is monitored at 405 nM in a microtiter plate reader for 30 minutes. The IC50s [sic] are then determined from the maximum gradients.

Calpain I and II Test

The testing of the inhibitory properties of calpain inhibitors is carried out in buffer using 50 mM tris HCl, pH 7.5; 0.1 M NaCl; 1 mM dithiotreithol [sic]; 0.11 mM CaCl₂, the fluorogenic calpain substrate Suc-Leu-Tyr-AMC (25 mM dissolved in DMSO, Bachem/Switzerland) being used. Human µ-calpain is isolated from erythrocytes and, after several chromatographic steps (DEAE-Sepharose, phenyl-Sepharose, Superdex 200 and Blue Sepharose), enzyme having a purity of >95%, assessed according to SDS-PAGE, Western blot analysis and N-terminal sequencing, is obtained. The fluorescence of the cleavage product 7-amino-4-methylcoumarin (AMC) is monitored in a Spex-Fluorolog fluorimeter at $\lambda_{ex}$=380 nm and $\lambda_{em}$=460 nm. In a measuring range of 60 min, the cleavage of the substrate is linear and the autocatalytic activity of calpain is low if the experiments are carried out at temperatures of 12° C. The inhibitors and the calpain substrate are added to the experimental batch as DMSO solutions, where DMSO should not exceed 2% in the final concentration.

In an experimental batch, 10 µl of substrate (250 µM final) and then 10 µl of µ-calpain (2 µg/ml final, i.e. 18 nM) are added to a 1 ml cuvette which contains buffer. The calpain-mediated cleavage of the substrate is measured for 15–20 min. 10 µl of inhibitor (50–100 µM solution in DMSO) are then added and the inhibition of the cleavage is measured for a further 40 min.

Ki values are determined according to the classical equation for reversible inhibition:

Ki [sic]=I/($v_0/v_i$)−1; where I=inhibitor concentration, $v_0$=initial velocity before addition The velocity is calculated from v=release of AMC/time, i.e. height/time.

Calpain is an intracellular cysteine protease. Calpain inhibitors must pass through the cell membrane in order to prevent the breakdown of intracellular proteins by calpain. Some known calpain inhibitors, such as, for example, E 64 and leupeptin, only cross the cell membranes with difficulty and accordingly show, although they are good calpain inhibitors, only a poor action in cells. The aim is to find compounds having better membrane accessibility. As a demonstration of the membrane accessibility of calpain inhibitors, we use human platelets.

Calpain-mediated Breakdown of Tyrosine Kinase pp60src [sic] in Platelets

After the activation of platelets, the tyrosine kinase $pp60^{src}$ is cleaved by calpain. This was investigated in detail by Oda et al. in *J. Biol. Chem.*, 1993, 268, 12603–12608. It was shown in this context that the cleavage of pp60src [sic] can be prevented by calpeptin, an inhibitor of calpain. The cellular effectiveness of our substances was tested following this publication. Fresh human blood treated with citrate was centrifuged at 200 g for 15 min. The platelet-rich plasma was pooled and diluted 1:1 with platelet buffer (platelet buffer: 68 mM NaCl, 2.7 mM KCl, 0.5 mM MgCl₂×6 H₂O, 0.24 mM NaH₂PO₄×H₂O, 12 mM NaHCO₃, 5.6 mM glucose, 1 mM EDTA, pH 7.4). After a centrifugation and washing step with platelet buffer, the platelets were adjusted to 107 [sic] cells/ml. The isolation of the human platelets was carried out at RT.

In the test batch, isolated platelets (2×106 [sic]) were preincubated at 37° C. with different concentrations of inhibitors (dissolved in DMSO) for 5 min. The platelets were then activated with 1 µM ionophore A23187 and 5 mM CaCl₂. After incubation for 5 min, the platelets were briefly centrifuged at 13000 rpm and the pellet was taken up in SDS sample buffer (SDS sample buffer: 20 mM tris HCl, 5 mM EDTA, 5 mM EGTA, 1 mM DTT, 0.5 mM PMSF, 5 µg/ml leupeptin, 10 µg/ml pepstatin, 10% glycerol and 1% SDS). The proteins were separated in a 12% strength gel and pp60src [sic] and its 52 kDa and 47 kDa cleavage products were identified by Western blotting. The polyclonal rabbit antibody anti-Cys-src (pp60src [sic]) used was purchased from the company Biomol Feinchemikalien (Hamburg). This primary antibody was detected using an HRP-coupled second antibody from goats (Boehringer Mannheim, FRG). The Western blotting was carried out according to known methods. The quantification of the cleavage of pp60src [sic] was carried out by densitometry, the controls used being nonactivated platelets (control 1: no cleavage) and platelets treated with ionophore and calcium (control 2: corresponds to 100% cleavage). The $ED_{50}$ value corresponds to the concentration of inhibitor at which the intensity of the color reaction is reduced by 50%.

Glutamate-induced Cell Death in Cortical Neurones

The test was carried out as in Choi D. W., Maulucci-Gedde M. A. and Kriegstein A. R., "Glutamate neurotoxicity in cortical cell culture". *J. Neurosci.* 1989, 7, 357–368. The halves of the cortex of 15 day-old mouse embryos were dissected and the individual cells were obtained enzymatically (trypsin). These cells (glia and cortical neurons) are inoculated into 24-well plates. After three days (laminin-coated plates) or seven days (ornithine-coated plates), the mitosis treatment is carried out using FDU (5-fluoro-2-deoxyuridine). 15 days after the cell preparation, cell death is induced by addition of glutamate (15 minutes). After the removal of glutamate, the calpain inhibitors are added. 24 hours later, the cell damage is determined by means of the determination of lactate dehydrogenase (LDH) in the cell culture supernatant.

It is postulated that calpain also plays a part in apoptotic cell death (M. K. T. Squier et al. *J. Cell. Physiol.* 1994, 159, 229–237; T. Patel et al. *Faseb Journal* 1996, 590, 587–597). Therefore, in a further model, cell death was induced with calcium in the presence of a calcium ionophore in a human cell line. Calpain inhibitors must pass into the cell and inhibit calpain there in order to prevent the induced cell death.

Calcium-mediated Cell Death in NT2 Cells

Cell death can be induced in the human cell line NT2 by means of calcium in the presence of the ionophore A 23187. 105 [sic] cells/well were plated out into microtiter plates 20 hours before the experiment. After this period, the cells were incubated with various concentrations of inhibitors in the presence of 2.5 $\mu$M ionophore and 5 mM calcium. 0.05 ml of XTT (cell proliferation kit II, Boehringer Mannheim) was added to the reaction batch after 5 hours. The optical density is determined approximately 17 hours later, according to the instructions of the manufacturer, in the Easy Reader EAR 400 from the company SLT. The optical density at which half of the cells have died is calculated from the two controls with cells without inhibitors, which were incubated in the absence and presence of ionophore.

In a number of neurological diseases or psychological disorders, increased glutamate activity, which leads to states of overstimulation or toxic effects in the central nervous system (CNS), occurs. Glutamate mediates its effects by means of various receptors. Two of these receptors are classified by the specific agonists NMDA receptor and AMPA receptor. Antagonists against these glutamate-mediated effects can thus be employed for the treatment of these diseases, in particular for therapeutic administration against neurodegenerative diseases such as Huntington's chorea and Parkinson's disease, neurotoxic disorders after hypoxia, anoxia, ischemia and after lesions, such as occur after stroke and trauma, or alternatively as antiepileptics (cf. *Arzneim. Forschung* 1990, 40, 511–514; TIPS, 1990, 11, 334–338; *Drugs of the Future* 1989, 14, 1059–1071).

Protection against cerebral overstimulation by excitatory amino acids (NMDA or AMPA antagonism in mice)

As a result of intracerebral administration of excitatory amino acids (EAA), such a massive overstimulation is induced that in a short time this leads to spasms and to the death of the animals (mice). These symptoms can be inhibited by systemic, e.g. intraperitoneal, administration of centrally active compounds (EAA antagonists). Since the excessive activation of EAA receptors of the central nervous system plays an important part in the pathogenesis of various neurological disorders, a conclusion can be drawn from the demonstrated EAA antagonism in vivo regarding a possible therapeutic utility of the substances against CNS disorders of this type. As a measure of the efficacy of the substances, an $ED_{50}$ value was determined at which 50% of the animals become symptom-free as a result of a fixed dose of either NMDA or AMPA as a result of the prior i.p. administration of the standard substance.

The heterocyclically substituted amides I are inhibitors of cysteine derivatives such as calpain I or II and cathepsin B or L and can thus be used for the control of diseases which are associated with an increased enzyme activity of the calpain enzymes or cathepsin enzymes. The present amides I can accordingly be used for the treatment of neurodegenerative diseases which occur after ischemia, damage by reperfusion after vascular occlusion trauma, subarachnoid hemorrhages and stroke, and of neurodegenerative diseases such as multiple infarct dementia, Alzheimer's disease, Huntington's disease and of epilepsies and furthermore for the treatment of damage to the heart after cardiac ischemias, damage to the kidneys after renal ischemias, skeletal muscle damage, muscular dystrophies, damage which occurs due to proliferation of the smooth muscle cells, coronary vasospasms, cerebral vasospasms, cataracts of the eyes, restenosis of the bloodstreams after angioplasty. Moreover, the amides I can be useful in the chemotherapy of tumors and metastasis thereof and for the treatment of diseases in which an increased interleukin-1 level occurs, such as in inflammations and rheumatic disorders.

In addition to the customary pharmaceutical auxiliaries, the pharmaceutical preparations according to the invention contain a therapeutically efficacious amount of the compounds I.

For local external application, for example in powders, ointments or sprays, the active compounds can be contained in the customary concentrations. As a rule, the active compounds are contained in an amount from 0.001 to 1% by weight, preferably 0.001 to 0.1% by weight.

In the case of internal administration, the preparations are administered in individual doses. 0.1 to 100 mg are provided in an individual dose per kg of body weight. The preparation can be administered daily in one or more doses depending on the nature and severity of the disorders.

According to the desired type of administration, the pharmaceutical preparations according to the invention contain the customary excipients and diluents in addition to the active compound. For local external application, pharmaceutical auxiliaries such as ethanol, isopropanol, ethoxylated castor oil, ethoxylated hydrogenated castor oil, polyacrylic acid, polyethylene glycol, polyethylene glyco [sic] stearate, ethoxylated fatty alcohols, paraffin oil, petroleum jelly and wool fat can be used. For internal administration, for example, lactose, propylene glycol, ethanol, starch, talc and polyvinylpyrrolidone are suitable.

Antioxidants such as tocopherol and butylated hydroxyanisole as well as butylated hydroxytoluene, flavor-enhancing additives, stabilizers, emulsifiers and lubricants can additionally be contained.

The substances contained in the preparation in addition to the active compound and the substances used in the production of the pharmaceutical preparations are toxicologically acceptable and compatible with the respective active compound. The pharmaceutical preparations are prepared in a customary manner, for example by mixing the active compound with other customary excipients and diluents.

The pharmaceutical preparations can be administered in various administration procedures, for example, orally, parenterally such as intravenously by infusion, subcutaneously, intraperitoneally and topically. Thus, preparation forms such as tablets, emulsions, infusion and injection solutions, pastes, ointments, gels, creams, lotions, powders and sprays are possible.

EXAMPLES

Example 1

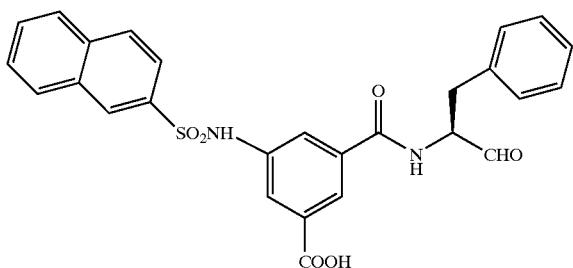

(S)-3-Carboxy-5-(2-naphthylsulfonamido)-N-(3-phenylpropan-1-al-2-yl)benzamide a) (S)-3-(Ethoxycarbonyl-5-nitro-N-(3-phenylpropan-1-ol-2-yl)benzamide 10 g (41.8 mmol) of monoethyl 5-nitroisophthalate, 6.3 g (41.8 mmol) of (S)-phenylalaninol and 10.6 g (104.5 mmol) of triethylamine were dissolved in 200 ml of methylene chloride at room temperature and stirred for 30 minutes. 1.9 g (13.9 mmol) of 1-hydroxybenzotriazole and subsequently, in portions, 8 g (41.6 mmol) of (N-dimethylaminopropyl)-N-ethylcarbodiimide were then added with ice-cooling. The entire mixture was stirred at room temperature for 16 hours. The reaction batch was diluted with methylene chloride to twice the volume using methylene chloride and washed successively with 2 M hydrochloric acid, water, 2 M sodium hydroxide solution and water again. The organic phase was separated off, dried and concentrated in vacuo. 9.1 g of the intermediate were obtained.

b) (S)-5-Amino-3-ethoxycarbonyl-N-(3-phenylpropan-1-ol-2-yl)benzamide 9 g (24.3 mmol) of the intermediate 1a were dissolved in 300 ml of ethanol and hydrogenated after addition of 1 g of palladium/carbon (10% strength). The reaction batch was then filtered and the filtrate was concentrated in vacuo. 8.1 g of the intermediate were obtained.

c) (S)-3-Ethoxycarbonyl-5-(2-naphthylsulfonamido)-N-(3-phenylpropan-1-ol-2-yl)benzamide 2 g (5.84 mmol) of the intermediate 1b and 2.4 ml (17.4 mmol) of triethylamine were dissolved in 50 ml of tetrahydrofuran. A solution of 1.32 g (5.82 mmol) of 2-naphthalenesulfonyl chloride in 30 ml of tetrahydrofuran was then added dropwise at 0° C. and the reaction batch was then stirred at 40° C. for 8 h. The reaction batch was then concentrated in vacuo and the residue was partitioned between water and ethyl acetate. The ethyl acetate phase was additionally washed with 2 M hydrochloric acid and water and then dried and concentrated in vacuo. The residue thus obtained was purified by chromatography on silica gel (eluent: methylene chloride/ethanol=20/1), 0.65 g of the intermediate being obtained.

d) (S)-3-Carboxy-5-(2-naphthylsulfonamido)-N-(3-phenylpropan-1-ol-2-yl)benzamide 0.65 g (1.2 mmol) of the intermediate 1c was dissolved in 30 ml of tetrahydrofuran and treated with 0.15 g (6.3 mmol) of lithium hydroxide, dissolved in 15 ml of water. The entire mixture was stirred at room temperature for 26 hours. The organic solvent was then removed in vacuo and the aqueous residue was acidified using 2 M hydrochloric acid. The precipitate obtained was filtered off with suction and dried. 0.46 g of the intermediate were obtained.

e) (S)-3-carboxy-5-(2-naphthylsulfonamido)-N-(3-phenylpropan-1-al-2-yl)benzamide 0.46 g (0.91 mmol) of the intermediate compound 1d and 0.37 g (3.65 mmol) of triethylamine were dissolved in 10 ml of dry dimethyl sulfoxide and treated with 0.44 g (2.76 mmol) of pyridine-sulfur trioxide complex. The entire mixture was stirred at room temperature for 16 h. The reaction mixture was then added to ice water, acidified with 1 M hydrochloric acid, and the precipitate was filtered off with suction. 0.36 g of the product was obtained.

$^1$H-NMR (D$_6$-DMSO): δ=2.9 (1H), 3.3 (1H), 4.5 (1H), 7.2 (5H), 7.6–7.9 (5H), 8.0–8.2 (4H), 8.5 (2H), 9.1 (1H), 9.6 (1H) and 10.9 (1H) ppm.

Example 2

N-(1-Carbamoyl-2-oxo-4-phenylpropan-2-yl)-3-carboxy-5-(2-naphthylsulfonamido)benzamide

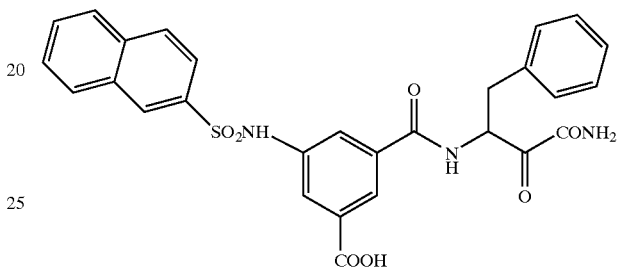

a) N-(1-Carbamoyl-2-hydroxy-4-phenylpropan-2-yl)-3-ethoxycarbonyl-5-nitrobenzamide 5.2 g (21.7 mmol) of monoethyl 5-nitroisophthalate, 5 g (21.7 mmol) of 3-amino-2-hydroxy-3-phenylbutyramide and 11.2 g (110.5 mmol) of triethylamine were dissolved in 200 ml of methylene chloride at room temperature and stirred for 30 minutes. 2.9 g (21.6 mmol) of 1-hydroxybenzotriazole and subsequently, in portions, 4.6 g (22.8 mmol) of (N-dimethylaminopropyl)-N-ethylcarbodiimide were then added with ice-cooling. The entire mixture was stirred at room temperature for 16 hours. The reaction batch was diluted to twice the volume using methylene chloride and washed successively with 2M hydrochloric acid, water, 2 M sodium hydroxide solution and water again. The organic phase was separated off, dried and concentrated in vacuo. 2.6 g of the intermediate were obtained.

b) 5-Amino-N-(1-carbamoyl-2-hydroxy-4-phenylpropan-2-yl)-3ethoxycarbonylbenzamide 2.6 g (6.25 mmol) of the intermediate 2a were dissolved in 50 ml of dimethylformamide, diluted with 200 ml of ethanol and hydrogenated after addition of 1 g of palladium/carbon (10% strength). The reaction batch was then filtered and the filtrate was concentrated in vacuo. 1.8 g of the intermediate were obtained.

c) N-(1-Carbamoyl-2-hydroxy-4-phenylpropan-2-yl)-3-ethoxycarbonyl-5-(2-naphthylsulfonamido)benzamide 1.8 g (4.7 mmol) of the intermediate 2b and a spatula tipful of 4-dimethylaminopyridine were dissolved in 30 ml of pyridine. 1.2 g (5.1 mmol) of naphthalenesulfonyl chloride were added dropwise at room temperature and the entire mixture was additionally stirred for 16 h. The reaction batch was then poured onto ice water and acidified with 2M hydrochloric acid. This aqueous phase was extracted several times with ethyl acetate. The combined organic phases were dried and concentrated in vacuo. The residue thus obtained was additionally treated successively with ether and a little ethyl acetate, 1.3 g of the intermediate being obtained.

(d) N-(1-Carbamoyl-2-hydroxy-4-phenylpropan-2-yl)-3-carboxy-5(2-naphthylsulfonamido)benzamide 1.25 g (2.2 mmol) of the intermediate 3c were dissolved in 10 ml of tetrahydrofuran and treated with 0.21 g (8.7 mmol) of lithium hydroxide, dissolved in 50 ml of water. The entire mixture was stirred at room temperature for 1 hour. The organic solvent was then removed in vacuo and the aqueous residue was acidified with 2M hydrochloric acid. The precipitate formed was filtered off with suction and dried. 1.0 g of the intermediate was obtained.

(e) N-(1-Carbamoyl-2-oxo-4-phenylpropan-2-yl)-3-carboxy-5-(2-naphthylsulfonamido)benzamide 0.9 g (1.6 mmol) of the intermediate compound 2 d and 1.4 ml (9.9 mmol) of triethylamine were dissolved in 25 ml of dry dimethyl sulfoxide and treated at room temperature with 0.78 g (4.9 mmol) of pyridine-sulfur trioxide complex, dissolved in 13 ml of dimethyl sulfoxide. The entire mixture was stirred at room temperature for 1 h. The reaction mixture was then poured onto ice water, acidified with 1M hydrochloric acid and the precipitate was filtered off with suction, 0.59 g of the product being obtained.

$^1$H-NMR (CF$_3$, COOD): δ=2.9 (1H), 3.1 (1H), 5.3 (1H), 7.0–8.3 (17H), 8.4 (1H) and 9.1 (1H) ppm.

The following examples can be prepared analogously to the above procedures:

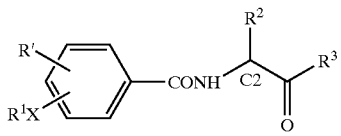

| Example | R' | R$^2$ | R$^3$ | R$^1$X |
|---|---|---|---|---|
| 2 | 3-COOH | (CH$_2$)$_3$CH$_3$ | CONH$_2$ | 5-Naphth-2-yl-SO$_2$NH |
| 3 | 3-COOH | CH$_2$Ph | H | 5-Phenyl-SO$_2$NH |
| 4 | 3-COOH | CH$_2$Ph | CONH$_2$ | 5-Phenyl-SO$_2$NH |
| 5 | 3-COOH | CH$_2$Ph | H | 5-n-Butyl-SO$_2$NH |
| 6 | 3-COOH | CH$_2$Ph | CONH$_2$ | 5-n-Butyl-SO$_2$NH |
| 7 | 4-COOH | CH$_2$Ph | H | 3-Phenyl-SO$_2$NH |
| 8 | 4-COOH | CH$_2$Ph | H | 5-Naphth-2-yl-SO$_2$NH |
| 9 | 4-COOH | CH$_2$Ph | CONH$_2$ | 5-Naphth-2-yl-SO$_2$NH |
| 10 | 4-COOH | CH$_2$Ph | H | 3-CH=CH-Phenyl |
| 11 | 4-COOH | CH$_2$Ph | H | 3-(Pyrid-2-yl) |
| 12 | 3-COOH | CH$_2$Ph | H | 4-CH=CH-Phenyl |

If R$^3$ = H, then the configuration of the C2 atom is (S); in the case of R$^3$ = CONH$_2$, this is (R.S).

| Example | R$^1$ | R$^2$ | R$^3$ | R$^1$x |
|---|---|---|---|---|
| 13 | 3-COOH | CH$_2$PH | CONH$_2$ | |
| 14 | 3-COOH | CH$_2$Ph | H | |
| 15 | 3-COOH | CH$_2$Ph | H | |
| 16 | 3-COOH | CH$_2$Ph | CONH$_2$ | |

-continued

| Example | R¹ | R² | R³ | R¹x |
|---|---|---|---|---|
| 17 | 3-COOH | CH₂Ph | H | 6,7-dimethoxy-benzo[g]quinazoline-2,4(1H,3H)-dione |
| 18 | 3-COOH | CH₂Ph | CONH₂ | 6,7-dimethoxy-benzo[g]quinazoline-2,4(1H,3H)-dione |
| 19 | 3-COOH | (CH₂)₃CH₃ | H | benzo[g]quinazoline-2,4(1H,3H)-dione |
| 20 | 3-COOH | (CH₂)₃CH₃ | CONH₂ | benzo[g]quinazoline-2,4(1H,3H)-dione |
| 21 | 3-COOH | CH₂Ph | CONH₂ | 2-(E)-2-(pyridin-4-yl)vinyl |
| 22 | 3-COOH | CH₂Ph | H | 2-(E)-2-(pyridin-4-yl)vinyl |
| 23 | 3-COOH | CH₂-cyclohexyl | H | 5-(naphthalen-2-yl-sulfonamide) |
| 24 | 3-COOH | CH₂-cyclohexyl | CONH₂ | 5-(naphthalen-2-yl-sulfonamide) |

-continued

| Example | R¹ | R² | R³ | R¹x |
|---|---|---|---|---|
| 25 | 3-COOH | CH₂Ph | H | 5-(quinolin-8-yl)SO₂NH |
| 26 | 3-COOH | CH₂Ph | CONH₂ | 5-(quinolin-8-yl)SO₂NH |
| 27 | 3-COOH | CH₂Ph | H | 5-(naphthalen-2-yl)CONH |
| 28 | 3-COOH | CH₂Ph | CONH₂ | 5-(naphthalen-2-yl)CONH |
| 29 | 4-COOH | CH₂Ph | CONH₂ | (E)-propenyl-naphthalene |
| 30 | 4-COOH | CH₂Ph | CONH₂ | (E)-propenyl-benzene |
| 31 | 4-COOH | CH₂Ph | CONH₂ | 2-(6-methylpyridyl) |
| 32 | 4-COOH | CH₂Ph | H | 2-(3-methylpyridyl) |
| 33 | 4-COOH | CH₂Ph | CONH₂ | 2-(pyrazinyl) |
| 34 | 3-COOH | CH₂Ph | CONH₂ | 2-pyridyl |
| 35 | 3-COOH | CH₂Ph | CONH₂ | (E)-propenyl-benzene |
| 36 | 3-COOH | CH₂Ph | CONH₂ | (E)-propenyl-naphthalene |

We claim:
1. An amide of formula I

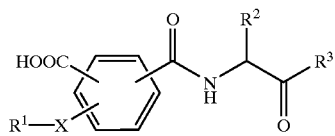

or a tautomeric or isomeric form, an enantiomeric or diastereomeric form, or a physiologically tolerable salt of the amide, wherein

- $R^1$ is $C_1$–$C_6$-alkyl, phenyl, naphthyl, quinolyl, pyridyl, pyrimidyl, pyridazyl, quinazolyl or quinoxalyl, where the rings are optionally substituted by up to 2 radicals $R^4$;
- $R^2$ is —$(CH_2)_m$—$R^8$, where $R^8$ is phenyl, cyclohexyl or indolyl and m=1 to 6;
- X is a bond, —$CH_2$—, —$CH_2CH_2$—, —CH=CH—, —C≡C—, —CONH—, —$SO_2$NH—, or
- $R^1$-X denotes

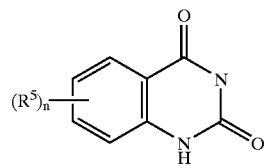

or

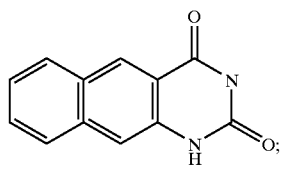

- $R^3$ is hydrogen or CO—$NR^6R^7$;
- $R^4$ is hydrogen, $C_1$–$C_4$-alkyl, which is branched or unbranched, or —O—$C_1$–$C_4$-alkyl;
- $R^5$ is hydrogen, $C_1$–$C_4$-alkyl, which is branched or unbranched, or —O—$C_1$–$C_4$-alkyl;
- $R^6$ is hydrogen, $C_1$–$C_6$-alkyl, which is branched or unbranched;
- $R^7$ is hydrogen, $C_1$–$C_6$-alkyl, which is branched or unbranched, and
- n is a number 0, 1 or 2.

2. The amide of formula I defined in claim 1, where
$R^1$ is phenyl, naphthyl, butyl or quinolyl,
$R^2$ is benzyl,
$R^3$ is hydrogen,
X is $SO_2$NH, and
$R^4$ is hydrogen.

3. The amide of formula I defined in claim 1, where
$R^1$ is phenyl, naphthyl, butyl or quinolyl,
$R^2$ is benzyl,
$R^3$ is $CONH_2$,
X is $SO_2$NH, and
$R^4$ is hydrogen.

* * * * *